US00PP25832P2

(12) United States Plant Patent
Suzuki

(10) Patent No.: US PP25,832 P2
(45) Date of Patent: Aug. 25, 2015

(54) ***LOROPETALUM* PLANT NAMED 'SPG-3-002'**

(50) Latin Name: *Loropetalum chinense*
Varietal Denomination: sPg-3-002

(71) Applicant: Yuji Suzuki, Kawaguchi (JP)

(72) Inventor: Yuji Suzuki, Kawaguchi (JP)

(73) Assignee: Southern Plant Group, Atlanta, GA (US)

( * ) Notice: Subject to any disclaimer, the term of this patent is extended or adjusted under 35 U.S.C. 154(b) by 185 days.

(21) Appl. No.: 13/987,778

(22) Filed: Aug. 31, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu
(74) *Attorney, Agent, or Firm* — C. A. Whealy

(57) ABSTRACT

A new and distinct cultivar of *Loropetalum* plant named 'sPg-3-002', characterized by its outwardly spreading and mounding plant habit; freely branching habit, dense and bushy plant form; dark burgundy and green-colored leaves; freely flowering habit; creamy white-colored flowers; and good container and garden performance.

3 Drawing Sheets

Botanical designation: *Loropetalum chinense.*
Cultivar denomination: 'sPg-3-002'.

BACKGROUND OF THE INVENTION

The present invention relates to a new and distinct *Loropetalum* plant, botanically known as *Loropetalum chinense* and hereinafter referred to by the name 'sPg-3-002'.

The new *Loropetalum* plant is a naturally-occurring whole plant mutation of an unnamed proprietary selection of *Loropetalum chinense*, not patented. The new *Loropetalum* plant was discovered and selected by the Inventor as a single plant within a population of plants of the unnamed proprietary selection in a controlled nursery environment in Kawaguchi City, Japan in 2003.

Asexual reproduction of the new *Loropetalum* plant by softwood vegetative cuttings in a controlled environment in Kawaguchi City, Japan since 2009 has shown that the unique features of this new *Loropetalum* plant are stable and reproduced true to type in successive generations.

SUMMARY OF THE INVENTION

Plants of the new *Loropetalum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'sPg-3-002'. These characteristics in combination distinguish 'sPg-3-002' as a new and distinct *Loropetalum* plant:

1. Outwardly spreading and mounding plant habit.
2. Freely branching habit, dense and bushy plant form.
3. Dark burgundy and green-colored leaves.
4. Freely flowering habit.
5. Creamy white-colored flowers.
6. Good container and garden performance.

Plants of the new *Loropetalum* can be compared to plants of the parent selection. Plants of the new *Loropetalum* differ from plants of the parent selection in flower color as plants of the parent selection have pink-colored flowers.

Plants of the new *Loropetalum* can be compared to plants of *Loropetalum chinense* 'Burgundy Blast', not patented. In side-by-side comparisons, plants of the new *Loropetalum* differed primarily from plants of 'Burgundy Blast' in flower color as plants of 'Burgundy Blast' have red purple-colored flowers.

BRIEF DESCRIPTION OF THE PHOTOGRAPHS

The accompanying colored photographs illustrate the overall appearance of the new *Loropetalum* plant showing the colors as true as it is reasonably possible to obtain in colored reproductions of this type. Colors in the photographs may differ slightly from the color values cited in the detailed botanical description which accurately describe the colors of the new *Loropetalum* plant.

The photograph on the first sheet is a side perspective view of a typical plant of 'sPg-3-002'.

The photograph on the second sheet is a close-up view of a typical plant of 'sPg-3-002'.

The photograph on the third sheet is a close-up view of a typical flowering plant of 'sPg-3-002'.

DETAILED BOTANICAL DESCRIPTION

The aforementioned photographs and following observations, measurements and values describe plants grown during the spring in three-gallon containers in an outdoor nursery in El Campo, Tex. and under cultural practices typical of commercial *Loropetalum* production. During the production of the plants, day temperatures averaged 27° C. and night temperatures averaged 14° C. Plants were two years old when the photographs and the description were taken. In the description, color references are made to The Royal Horticultural Society Colour Chart, 1995 Edition, except where general terms of ordinary dictionary significance are used.

Botanical classification: *Loropetalum chinense* 'SPg-3-002'.

Parentage: Naturally-occurring whole plant mutation of an unnamed proprietary selection of *Loropetalum chinense*, not patented.

Propagation:

*Type*.—By softwood vegetative cuttings.

*Time to initiate roots, summer*.—About 15 days at soil temperatures about 24° C.

*Time to initiate roots, winter*.—About 30 days at soil temperatures about 18° C.

*Time to produce a rooted young plant, summer*.—About 65 days at soil temperatures about 24° C.

*Time to produce a rooted young plant, winter*.—About 90 days at soil temperatures about 18° C.

*Root description*.—Medium in thickness, fibrous; purplish in color.

*Rooting habit*.—Moderately freely branching; medium density.

Plant description:

*Plant and growth habit*.—Perennial shrub; outwardly spreading and mounding plant habit; moderately vigorous growth habit; freely branching habit with lateral branches potentially develop at every node; dense and bushy plant form.

*Plant height*.—About 48.26 cm.

*Plant diameter* (*area of spread*).—About 86.36 cm.

Lateral branch description:

*Length*.—About 45.72 cm.

*Internode length*.—About 2 cm.

*Aspect*.—About 60° from vertical.

*Strength*.—Moderately strong; flexible.

*Texture*.—Pubescent.

*Color, immature*.—Close to 199A.

*Color, mature*.—Close to 197B.

Leaf description:

*Arrangement*.—Alternate, single.

*Length*.—About 3.5 cm to 4.5 cm.

*Width*.—About 2 cm to 2.5 cm.

*Shape*.—Ovate to obovate.

*Apex*.—Mucronate.

*Base*.—Slightly oblique.

*Margin*.—Entire.

*Texture, upper and lower surfaces*.—Pubescent; leathery.

*Venation pattern*.—Pinnate; arcuate.

*Color*.—Developing leaves, upper surface: Close to 200A. Developing leaves, lower surface: Close to 189A. Fully expanded leaves, upper surface: Close to 202A and 147A; venation, close to 147D. Fully expanded leaves, lower surface: Close to 138A; venation, close to 147D.

*Petioles*.—Length: About 4 mm. Diameter: About 1 mm. Texture, upper and lower surfaces: Pubescent; leathery. Color, upper and lower surfaces: Close to 189A.

Flower description:

*Flower arrangement and flowering habit*.—Single flowers arranged in clusters at terminal leaf axils; freely flowering habit with about six flowers per cluster; flowers face mostly outwardly.

*Natural flowering season*.—Early flowering habit, plants of the new *Loropetalum* begin flowering in March and April in Texas; flowers not persistent.

*Fragrance*.—None detected.

*Flower diameter*.—About 3 cm.

*Flower length* (*height*).—About 2 cm.

*Flower buds*.—Length: About 4 mm. Diameter: About 3 mm. Shape: Roughly spherical. Color: Close to 160D.

*Petals*.—Arrangement: Typically four petals in a single whorl. Length: About 1.5 cm. Width: About 2 mm. Shape: Lanceolate. Apex: Typically rounded. Base: Cuneate. Margin: Entire; slightly undulate. Texture: Smooth, glabrous; papery. Color: When opening, upper and lower surfaces: Close to 155A. Fully opened, upper and lower surfaces: Close to 155A.

*Sepals*.—Arrangement: Typically four sepals in a single whorl. Length: About 3 mm. Width: About 2 mm. Shape: Triangular. Apex: Acute. Base: Attenuate. Margin: Entire. Texture, upper and lower surfaces: Pubescent. Color, upper and lower surfaces: Close to 151A.

*Peduncles*.—Length: About 5 mm to 10 mm. Diameter: About 1 mm. Strength: Moderately strong, flexible. Texture: Pubescent. Color: Close to 152B.

*Reproductive organs*.—Androecium: Stamen number: About eight per flower. Filament length: Less than 1 mm. Filament color: Close to 155D. Anther shape: Oblong. Anther length: About 1 mm. Anther color: Close to 155D. Amount of pollen: Scarce. Pollen color: Close to 155D. Gynoecium: Pistil number: One to four per flower. Pistil length: About 1 mm. Style length: About 1 mm. Style color: Close to 151A. Stigma color: Close to 151A.

*Seeds*.—Quantity: About one or two seeds are produced per flower. Length: About 8 mm to 10 mm. Diameter: About 5 mm. Color: Close to 139C.

Garden performance: Plants of the new *Loropetalum* have been observed to have good garden performance and to tolerate wind, rain and temperatures ranging from about −10° C. to about 37° C.

Pathogen & pest resistance: Plants of the new *Loropetalum* have not been observed to be resistant to pathogens and pests common to *Loropetalum* plants.

It is claimed:

1. A new and distinct *Loropetalum* plant named 'sPg-3-002' as illustrated and described.

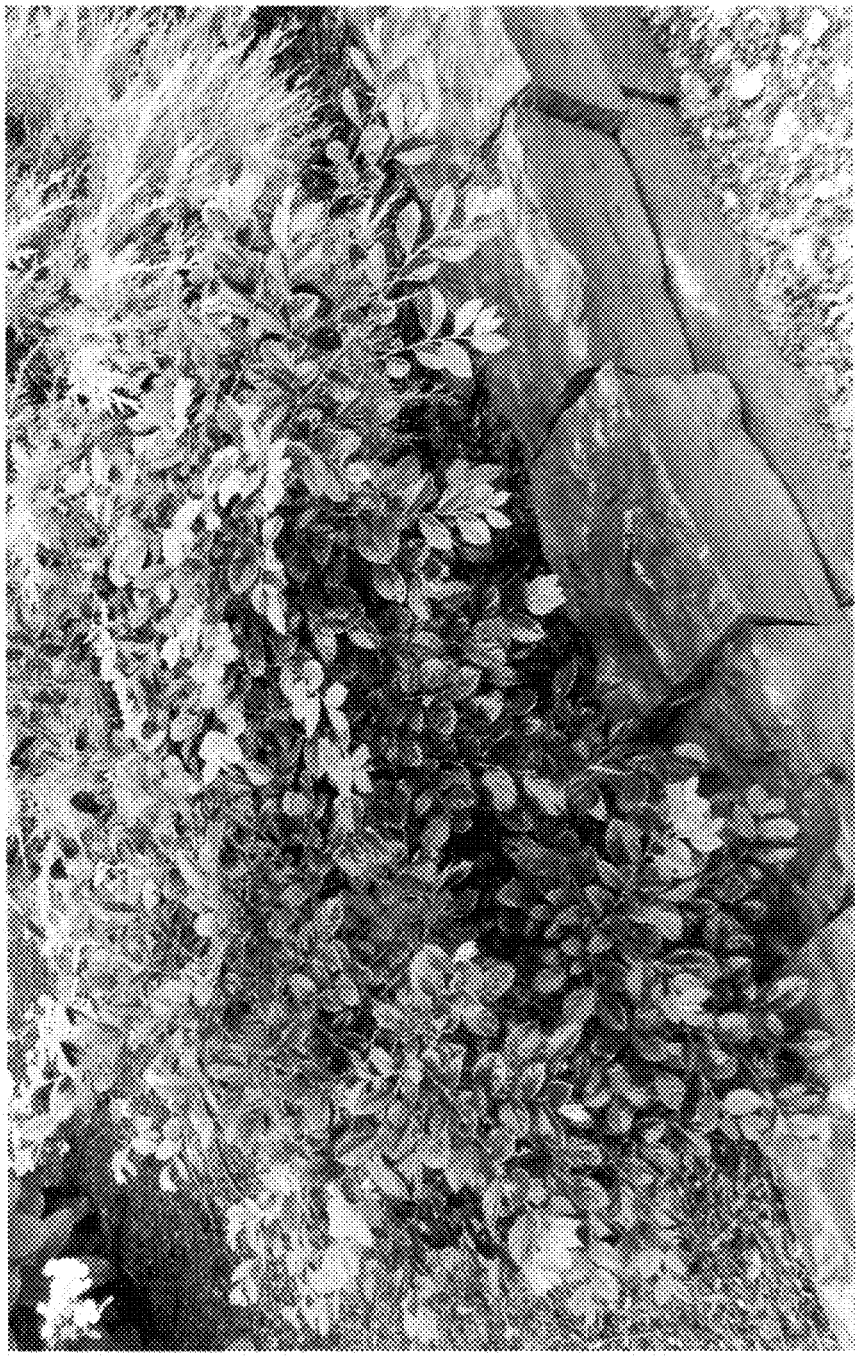

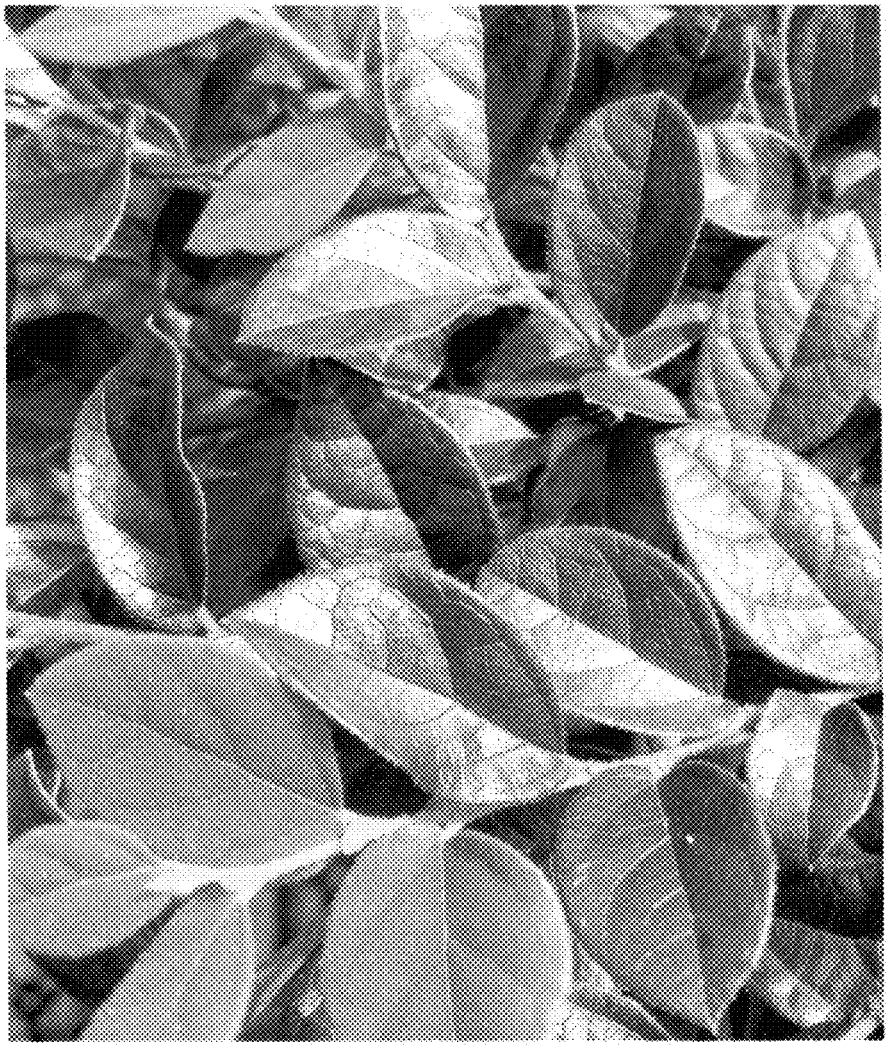

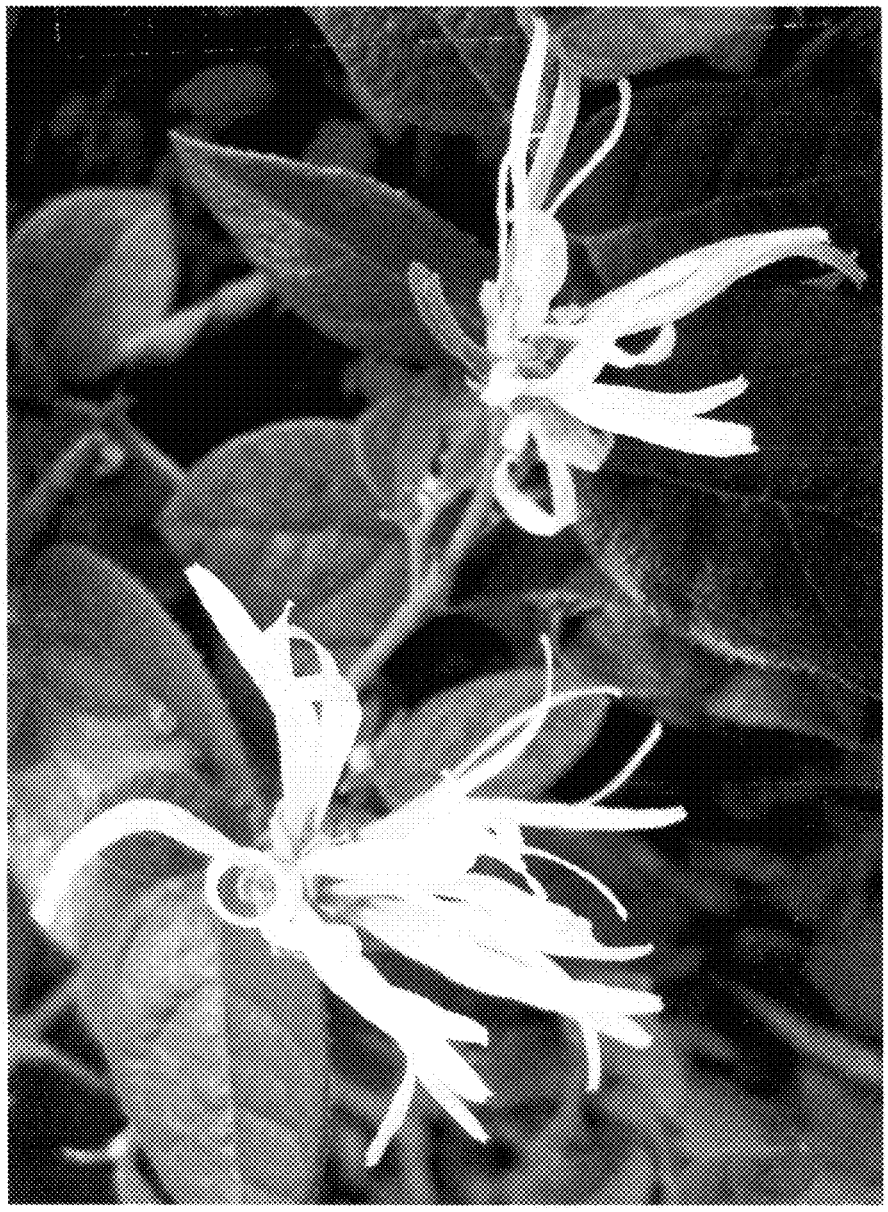

* * * * *